United States Patent [19]

Farkas et al.

[11] Patent Number: 5,837,159
[45] Date of Patent: Nov. 17, 1998

[54] CHEMICAL DETOXIFIER FOR EMBALMING SOLUTIONS

[76] Inventors: Gabriel J. Farkas, 9843 Forbes Ave., Northridge, Calif. 91343; Michel Iskarous, 659 Pierre Rd., Walnut, Calif. 91789

[21] Appl. No.: 717,908

[22] Filed: Sep. 23, 1996

[51] Int. Cl.⁶ .............................. A01N 1/00; C09K 3/00
[52] U.S. Cl. ...................... 252/193; 252/184; 252/190; 27/22.1; 27/22.2; 424/75
[58] Field of Search ..................... 27/22.1, 22.2; 424/75; 252/193, 184, 190

[56] References Cited

U.S. PATENT DOCUMENTS

| | | | |
|---|---|---|---|
| 3,360,492 | 12/1967 | Tsou | 260/29.4 |
| 3,382,197 | 5/1968 | Purcell | 260/17.4 |
| 3,400,079 | 9/1968 | Clifford et al. | 252/184 |
| 3,607,863 | 9/1971 | Dosch | 260/209 |
| 4,397,756 | 8/1983 | Lehmann | 252/182 |
| 4,443,354 | 4/1984 | Eian | 252/190 |
| 5,622,696 | 4/1997 | Camiener | 424/75 |

*Primary Examiner*—Sharon Gibson
*Assistant Examiner*—Deanna Baxam

[57] ABSTRACT

A chemical composition is disclosed herein for performing a complex neutralization and fixation of embalming fluids, providing a method for the rapid neutralization of formaldehyde vapors, the control of incidental releases, detoxification and disposal of unused or spent embalming fluids, and of any unused or spent aqueous or non-aqueous formaldehyde solutions. The composition includes alkanolamines for rapid reaction with formaldehyde vapors, aqueous and non-aqueous solutions of formaldehydes, for absorbing hydrogen sulfide and carbon dioxide from the air, and cyclodextrins for inclusion complexation of all the components of spent and/or unused embalming fluids.

2 Claims, No Drawings

CHEMICAL DETOXIFIER FOR EMBALMING SOLUTIONS

BACKGROUND OF THE INVENTION

1. Field of the Invention

The present invention relates to the field of detoxification and neutralization of hazardous substances, and more particularly to a novel chemical composition incorporating a combination of substances which are rapidly neutralizing toxic formaldehyde vapors released by embalming fluids, and by any aqueous and non-aqueous formaldehyde solutions, absorbing carbon dioxide and hydrogen sulfide from the air, detoxifying hazardous spent embalming fluids by neutralizing formaldehydes in aqueous and non-aqueous solutions, and molecularly encapsulating all the components of embalming fluids.

2. Brief Description of the Prior Art

Concentrated embalming fluids before being diluted to preparation solutions contain up to 36% formaldehydes w/v, glutaraldehydes, methanol, phenols, and possibly, anticoagulants, humectants and surfactants. But neutralizing products are available excusively for low concentrated formaldehydes. These compounds are intended for use with 10% formalin waste (3.75% formaldehyde w/v) only. The neutralization time is about 20 minutes. If 37% formaldehyde waste is to be neutralized, it must be diluted to 10% formalin before adding these neutralizers. Therefore a long-standing need existed to provide an unique neutralizer which not only detoxifies more concentrated formaldehyde solutions used in industrial and medical community operations, but encapsulates all components of embalming fluids, and modifies their chemical activity, converts these fluids to a non-hazardous material.

SUMMARY OF THE INVENTION

Accordingly, the above problems and difficulties are obviated by the present invention, which provides a chemical composition that detoxifies formaldehyde, chief component of the embalming fluids, modifies the chemical activity of all hazardous components of the embalming fluids by molecular encapsulation, complexation and stabilization. Therefore, it is among the primary objects of the present invention to provide a novel, fast reacting neutralizer of toxic formaldehyde vapors released during the employment of embalming fluids. Another object of the present invention is to provide a fast reacting neutralizer for the other hazardous components of embalming fluids. Yet another object of the present invention is to provide a fast reacting neutralizer for spent embalming fluids of various concentrations. Yet another object of the present invention is to provide a fast reacting neutralizer for incidental releases of embalming fluids of various concentrations. Yet another object of the present invention is to provide a cleaner indoor environment in embalming rooms. Yet another object of the present invention is to provide a fast reacting neutralizer of toxic formaldehyde vapors released by any unused or spent formaldehyde solutions of various concentrations. Still another object of the present invention is to provide a fast reacting neutralizer for incidental releases of unused or spent formaldehyde solutions of various concentrations.

DESCRIPTION OF THE PREFERRED COMPOSITION

The composition/formulation of the present invention which is believed to be novel is set forth with particularity in the appended claims. The present invention, both as to its organization and manner of operation, together with further objects and advantages thereof, may best be understood with reference to the following description. Two alkanolamines, 2-amino-2 ethyl-1,3 propanediol (AEPD), and tris (hydroxymethyl) Amninomethane (Tris Amino), in aqueous solution, are employed for rapid neutralization of formaldehyde vapors, aqueous and non-aqueous formaldehyde solutions of various concentrations. These substances are well suited for this application because each consumes two molecules of formaldehyde per mole of amine. Urea is used as additional neutralizer, the urea lattice is a strong host for formaldehydes. Cyclodextrins used for inclusion complexation for all the components, including formaldehyde, of embalming fluids, are a group of cavity-containing cyclic compounds, and provide a method of molecularly encapsulating, and thereby modifying the apparent physical and chemical properties of the guest molecules, giving rise to beneficial modifications of guest molecules not otherwise achievable:

1. Solubility enhancement
2. Stabilization of guests against oxidation, visible or ultraviolet light, and heat
3. Physical insulation of incompatible substances.

The cyclodextrins are a class of cavity-containing cyclic compounds possessing the property of forming a special type of complex known as a molecular inclusion/encapsulation complex. Such complexes include entrapped molecules, known as the Guest, within the complexing agent which is known as the Host. The potential guest list for molecular inclusion includes aldehydes, alcohols, organic acids, fatty acids, aromatics, gases, and polar guests such as oxy-acids and amines. A particular formulation of the present invention for detoxifying the embalming solution used for frozen corpses (fluid of the highest concentration used in embalming processes) is the following:

For 100 mL aqueous solution:
1.0 gram beta-cyclodextrin
8.0 grams Tris Amino
11.0 grams AEPD
6.0 grams urea

What is claimed is:

1. A composition for use in rapid detoxification of toxic formaldehyde vapors and absorbtion of hydrogen sulfide and carbon dioxide from incidental releases of unused or spent embalming solutions of various concentrations, comprising tris(hydroxymethyl) aminomethane and 2-amino-2-ethyl-1, 3-propanediol and beta-cyclodextrin.

2. The composition of claim 1, which further comprises urea, for use in rapid detoxification (neutralization time is less than five minutes) of formaldehydes in unused and/or spent embalming solutions of different concentrations.

* * * * *